US012245881B2

(12) United States Patent
Wang et al.

(10) Patent No.: US 12,245,881 B2
(45) Date of Patent: Mar. 11, 2025

(54) ASSISTANCE SYSTEM AND METHOD FOR SUSPENSION DEVICE, AND X-RAY IMAGING SYSTEM

(71) Applicant: GE Precision Healthcare LLC, Wauwatosa, WI (US)

(72) Inventors: Chunyu Wang, Beijing (CN); Yuqing Li, Beijing (CN); Jinfeng Wang, Beijing (CN); Jie Liu, Beijing (CN); Chuanfu Zhang, Beijing (CN); Peng Zhao, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 294 days.

(21) Appl. No.: 17/896,855

(22) Filed: Aug. 26, 2022

(65) Prior Publication Data

US 2023/0071435 A1 Mar. 9, 2023

(30) Foreign Application Priority Data

Sep. 3, 2021 (CN) .......................... 202111035558.X

(51) Int. Cl.
*A61B 6/00* (2024.01)
*A61B 6/46* (2024.01)
*A61B 6/58* (2024.01)

(52) U.S. Cl.
CPC .......... *A61B 6/4482* (2013.01); *A61B 6/4464* (2013.01); *A61B 6/4476* (2013.01);
(Continued)

(58) Field of Classification Search
CPC ... A61B 6/4482; A61B 6/4464; A61B 6/4476; A61B 6/467; A61B 6/54; A61B 6/582; A61B 6/547; G01L 5/22; G01L 5/0066
See application file for complete search history.

(56) References Cited

U.S. PATENT DOCUMENTS 8,755,492 B2 6/2014 Lee
2006/0207419 A1* 9/2006 Okazaki .................. F15B 11/20
  91/35
2013/0025055 A1* 1/2013 Saracen ............... A61N 5/1049
  901/29

(Continued)

FOREIGN PATENT DOCUMENTS

EP 3075317 B1 9/2017
JP 2011125580 A 6/2011

*Primary Examiner* — Dani Fox
*Assistant Examiner* — Mamadou Faye

(57) ABSTRACT

Provided in the present application are an assistance system and method for a suspension device, and an X-ray imaging system. The suspension device includes a tube device, a tube controller, a motion driving device and an assistance system. The motion driving device is capable of driving the suspension device to move along a first coordinate system. The assistance system includes a measurement device and a control device. The measurement device is disposed between the tube device and the tube controller so as to obtain an initial force of an operator, wherein the initial force includes the magnitude and direction of a force along a second coordinate system in which the measurement device is located. The control device includes a calibration unit and a calculation unit. The calibration unit is used for calibrating the initial force to obtain a calibrated force. The calculation unit is used for performing a coordinate transformation on the calibrated force to obtain a torque value corresponding to the first coordinate system, and sending the torque value to the motion driving device to enable the motion driving device to provide assistance on the basis of the torque value.

12 Claims, 7 Drawing Sheets

(52) U.S. Cl.
CPC ................ *A61B 6/467* (2013.01); *A61B 6/54* (2013.01); *A61B 6/582* (2013.01)

(56) References Cited

U.S. PATENT DOCUMENTS

2019/0327394 A1* 10/2019 Ramirez Luna ....... H04N 23/51
2020/0094693 A1* 3/2020 Caro Suarez ........... B60L 15/20

* cited by examiner

ASSISTANCE SYSTEM AND METHOD FOR SUSPENSION DEVICE, AND X-RAY IMAGING SYSTEM

CROSS REFERENCE

The present application claims priority and benefit of Chinese Patent Application No. 202111035558.X filed on Sep. 3, 2021, which is incorporated herein by reference in its entirety.

TECHNICAL FIELD

The present invention relates to medical imaging technology, and more specifically to an assistance system and method for a suspension device, and an X-ray imaging system.

BACKGROUND

In an X-ray imaging system, radiation from an X-ray source is emitted toward an object under examination, and the object is usually a patient in a medical diagnosis application. A part of the radiation passes through the object under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display device of the X-ray imaging system.

Conventional ceiling-mounted overhead tube suspension (OTS) usually includes motions of five axes. The suspension device can move along three axes in a room-based coordinate system. The tube device can rotate in a horizontal plane and a vertical plane. The suspension device can be configured in different modes such as a fully manual mode, a five-axis fully automatic mode, a four-axis automatic mode or a three-axis automatic mode.

Even for the five-axis fully automatic mode, when a motor drives the suspension device to move a predetermined distance, a user will choose to manually operate the suspension device in order to perform fine adjustments when an object under examination changes positions or due to some other reasons that require fine adjustments of the tube position, or when only fine adjustments of the tube device are required for the next object under examination. However, the suspension device is particularly heavy, and the user needs to use great force to operate the suspension device, and for hospitals with particularly high demand for examination or filming, the high-frequency manual operation will cause great strain to the user.

SUMMARY

Provided in the present invention are an assistance system and method for a suspension device, and an X-ray imaging system.

Exemplary embodiments of the present invention provide an assistance system for a suspension device. The suspension device comprises a tube device, a tube controller, a motion driving device and the assistance system. The motion driving device is capable of driving the suspension device to move along a first coordinate system. The assistance system comprises a measurement device and a control device. The measurement device is disposed between the tube device and the tube controller so as to obtain an initial force of an operator, wherein the initial force comprises the magnitude and direction of a force along a second coordinate system in which the measurement device is located. The control device comprises a calibration unit and a calculation unit. The calibration unit is used for calibrating the initial force to obtain a calibrated force. The calculation unit is used for performing a coordinate transformation on the calibrated force to obtain a torque value corresponding to the first coordinate system, and sending the torque value to the motion driving device to enable the motion driving device to provide assistance on the basis of the torque value.

Specifically, the motion driving device comprises an automatic mode and an assistance mode, and the assistance system further comprises a mode-switching device disposed on the tube controller to switch the motion driving device between the automatic mode and the assistance mode.

Specifically, the mode-switching device comprises a plurality of switch buttons, and the plurality of switch buttons respectively correspond to movements along respective axes in the first coordinate system, so as to perform switching from the automatic mode to the assistance mode.

Specifically, the tube controller comprises a display screen and an operating handle, and the mode-switching device further comprises at least one sensor disposed at the bottom of the display screen or on the operating handle to switch the motion driving device from the automatic mode to the assistance mode when the operator operates the operating handle.

Specifically, each of the plurality of switch buttons comprises an indicator light, and when at least one of the switch buttons is pressed by an operator, the indicator light illuminates to indicate such pressing, and when the operating handle is operated by an operator, all of the indicator lights of the plurality of switch buttons illuminate to indicate such operation.

Specifically, the calibration unit is further used for calibrating the initial force on the basis of a current first rotation angle and a current second rotation angle and according to a look-up table, so as to obtain the calibrated force, the first rotation angle being an angle at which the tube rotates in a vertical plane, and the second rotation angle being an angle at which the tube rotates in a horizontal plane.

Specifically, the calibration unit further comprises limiting the calibrated force on the basis of a real-time feedback value of the motion driving device and performing a coordinate transformation on the limited calibrated force, the real-time feedback value comprising at least one of a movement speed and a position of the suspension device.

Specifically, the calculation unit is further used for performing a coordinate transformation on the basis of a positional relationship between the first coordinate system and the second coordinate system.

Specifically, the positional relationship between the first coordinate system and the second coordinate system comprises a matrix related to the first rotation angle and the second rotation angle.

Specifically, the torque value comprises the product of a force obtained after a coordinate transformation and a multiplier, the multiplier being adjustable.

Specifically, the calculation unit is further used for performing slope-limiting on a transformed force obtained after the coordinate transformation, and the torque value comprises the product of a force obtained after the slope-limiting and a multiplier.

The exemplary embodiments of the present invention further provide an X-ray imaging system, and the system comprises the aforementioned assistance system for the suspension device.

The exemplary embodiments of the present invention further provide an assistance method for a suspension device. The suspension device comprises a motion driving device. The assistance method comprises: obtaining an initial force applied by an operator to the suspension device; switching the motion driving device to an assistance mode on the basis of the initial force; calibrating the initial force to obtain a calibrated force; performing a coordinate transformation on the calibrated force to obtain a torque value corresponding to a first coordinate system relating to an initial position of the suspension device; and controlling the motion driving device to operate to provide assistance on the basis of the torque value.

Specifically, the calibration comprises calibrating the initial force according to a look-up table on the basis of a first rotation angle and a second rotation angle of the current suspension device.

Specifically, the coordinate transformation comprises a coordinate transformation on the basis of a positional relationship between the first coordinate system and the second coordinate system.

Specifically, the positional relationship between the first coordinate system and the second coordinate system comprises a matrix related to the first rotation angle and the second rotation angle.

Specifically, obtaining the torque value comprises multiplying a force obtained after a coordinate transformation and a multiplier, the multiplier being adjustable.

Specifically, the assistance method further comprises limiting the calibrated force on the basis of a real-time feedback value from the motion driving device, and performing a coordinate transformation on the limited calibrated force.

Specifically, the assistance method further comprises performing slope-limiting on a transformed force obtained after the coordinate transformation.

Other features and aspects will become apparent from the following detailed description, accompanying drawings, and claims.

BRIEF DESCRIPTION OF THE DRAWINGS

The present invention can be better understood through the description of exemplary embodiments of the present invention in conjunction with the accompanying drawings, in which.

DETAILED DESCRIPTION

Specific implementations of the present invention will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present invention, some design, manufacture or production changes based on the technical content disclosed in the present disclosure are only common technical means, and should not be construed as insufficient content of the present disclosure.

Unless defined otherwise, technical terms or scientific terms used in the claims and specification should have usual meanings understood by those of ordinary skill in the technical field to which the present invention belongs. The terms "first," "second," and similar terms used in the description and claims of the patent application of the present invention do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article in front of "include" or "comprise" encompass elements or articles and their equivalent elements listed after "include" or "comprise", and do not exclude other elements or articles. The term "connect" or "connected" and similar words are not limited to physical or mechanical connections, and are not limited to direct or indirect connections.

Figure 1:
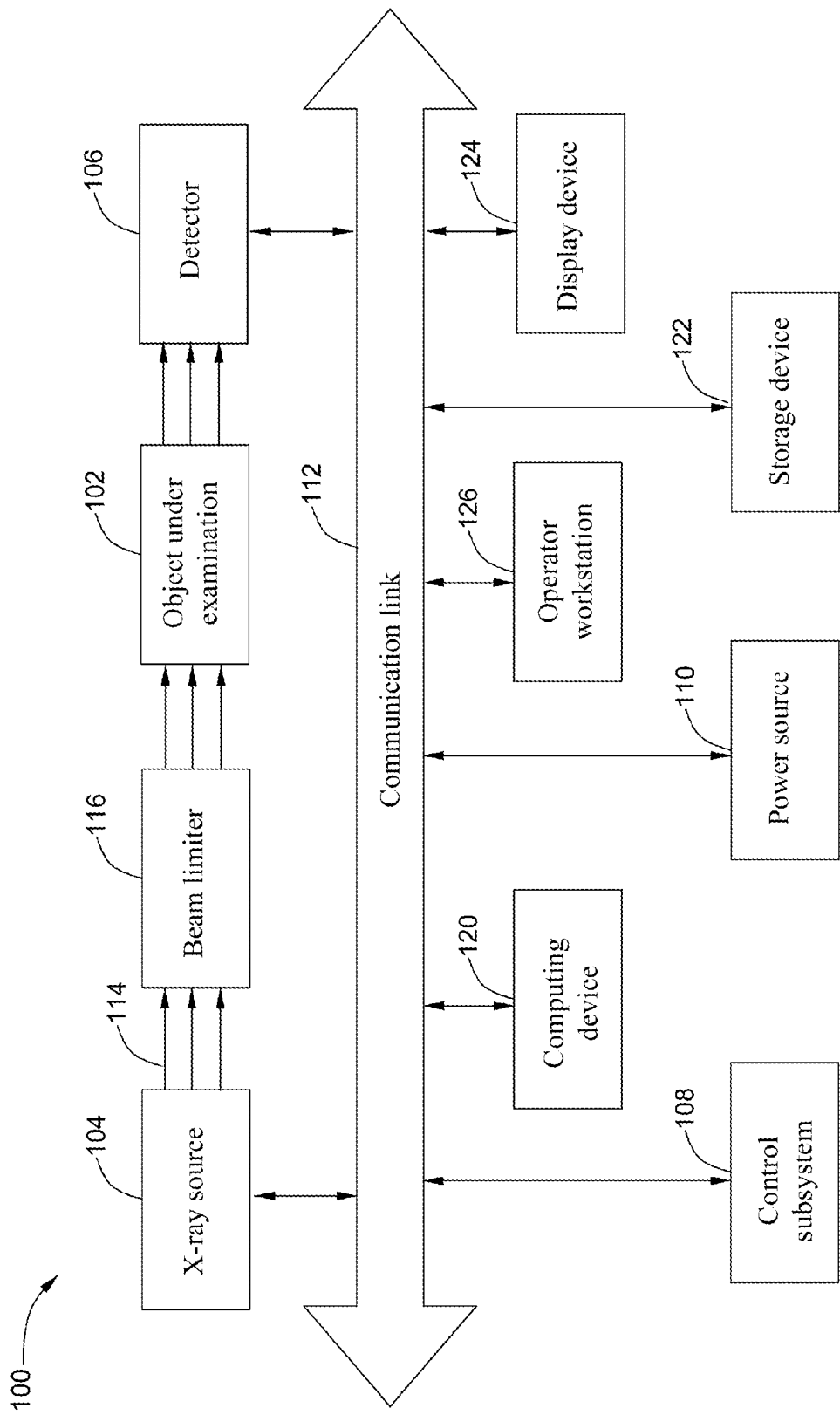
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes an X-ray source 104, a detector 106 and a control subsystem 108. In some embodiments, the X-ray imaging system 100 may be a fixed X-ray imaging system disposed in a fixed X-ray imaging room, or may be a mobile X-ray imaging system.

The X-ray source 104 can project X-rays 114 onto an expected region of interest in an object under examination 102. Specifically, the X-ray source 104 may be positioned adjacent to a beam limiter 116, and the beam limiter 116 is configured to align the X-rays 114 to the expected region of interest in the object under examination 102. At least part of the X-rays 114 may be attenuated through the object under examination 102 and may be incident on the detector 106.

The control subsystem 108 includes a source controller (not shown in the figure) and a detector controller (not shown in the figure). The source controller is configured to instruct the X-ray source 104 to emit X-rays 114 for image exposure. The detector controller is configured to coordinate control of various detector functions, such as executing various signal processing and filtering functions, specifically, configured to perform initial adjustment of a dynamic range, interleaving of digital image data, and the like. In some embodiments, the control subsystem 108 may provide power and timing signals for controlling the operation of the X-ray source 104 and the detector 106. Exactly speaking, the control subsystem 108 may provide power and timing signals to the X-ray source 104 and/or the detector 106 by using a power source 110 and one or a plurality of wired and/or wireless communication links 112, respectively, and the communication links 112 may correspond to a backplane bus, a local area network, a wide area network, and/or the Internet. In some embodiments, the power source 110 includes one or a plurality of batteries. In addition, although FIG. 1 shows that the power source 110 is connected to the X-ray source 104 through the communication link, those skilled in the art should understand that the power source 110 may also be directly coupled to the X-ray source 104.

The control subsystem 108 may be configured and/or arranged for use in different manners. For example, in some implementations, a single control subsystem 108 may be used. In other implementations, a plurality of control subsystems 108 are configured to work together (for example, configured on the basis of distributed processing) or separately, where each control subsystem 108 is configured to handle specific aspects and/or functions, and/or to process data used to generate a model used only for a specific X-ray imaging system. In some implementations, the control subsystem 108 may be local (for example, in the same place as one or a plurality of X-ray imaging systems 100, such as in the same facility and/or the same local network). In other implementations, the control subsystem 108 may be remote and thus can only be accessed via a remote connection (for example, via the Internet or other available remote access technologies). In a specific implementation, the control subsystem 108 may be configured in a cloud-like manner, and may be accessed and/or used in a manner substantially similar to that of accessing and using other cloud-based systems.

In some embodiments, the system 100 further includes a computing device 120. The computing device 120 may be configured to use digitized signals to reconstruct one or a plurality of required images and/or determine useful diagnostic information corresponding to the object under examination 102. The computing device 120 may include one or a plurality of dedicated processors, graphics processing units, digital signal processors, microcomputers, microcontrollers, application-specific integrated circuits (ASICs), field programmable gate array (FPGA) or other suitable processing devices.

In some embodiments, the system 100 further includes a storage device 122. The computing device 120 may store the digitized signals in the storage device 122. For example, the storage device 122 may include a hard disk drive, a floppy disk drive, a CD-read/write (CD-R/W) drive, a digital versatile disc (DVD) drive, a flash drive, and/or a solid-state storage device. The storage device is configured to store a program executable by a computer, and when the computer executes the program, a plurality of components of the X-ray imaging system are enabled to implement operations corresponding to the aforementioned imaging sequence. When the computer executes the program, an X-ray imaging method may also be performed to post-process the original image to obtain an optimized image after post-processing.

Although FIG. 1 illustrates the storage device 122, the computing device 120, and the control subsystem 108 as separate devices, in some embodiments, one or a plurality of them may be combined into a single device to effectively utilize the floor space and/or meet expected imaging requirements.

In one embodiment, the system 100 further includes a display device 124. The display device 124 can be configured to display a reconstructed image and/or diagnostic information, etc.

In one embodiment, the system 100 further includes an operator workstation 126. The operator workstation 126 allows the user to receive and evaluate the reconstructed image, and input a control instruction (an operation signal or a control signal). The operator workstation 126 may include a user interface (or a user input apparatus), such as a keyboard, a mouse, a voice-activated controller, or any other suitable input devices in the form of an operator interface. An operator may input an operation signal/control signal, for example, one or a plurality of scan parameters, to the control subsystem 108 by means of the user interface and/or request required diagnostic information and/or image to evaluate the internal structure and/or functionality of the object under examination 102.

Figure 2:
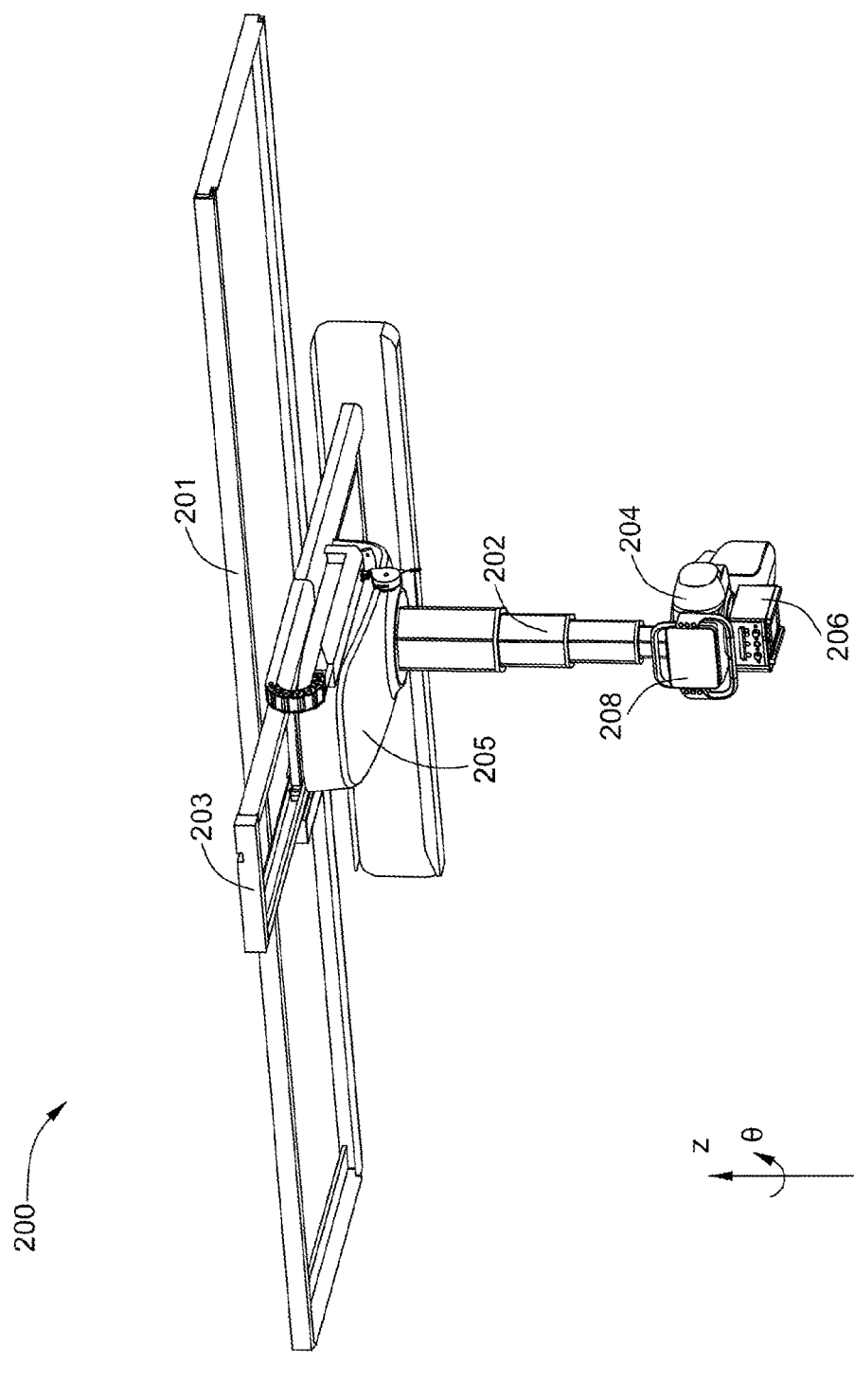
FIG. 2 is a schematic diagram of a suspension device according to some embodiments of the present invention.
Figure 3:
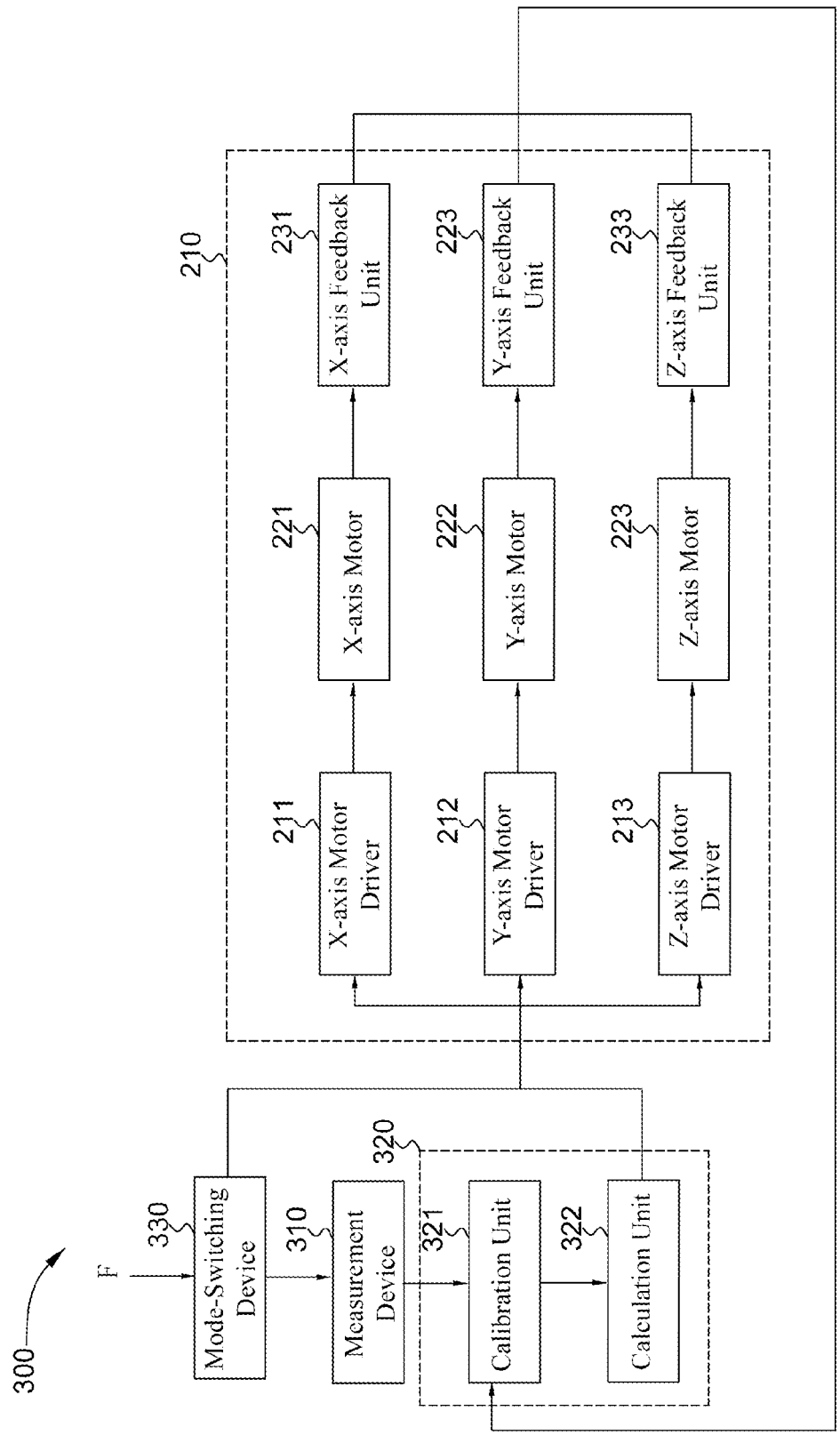
FIG. 3 is a schematic diagram of an assistance system for a suspension device according to some embodiments of the present invention.
Figure 4:
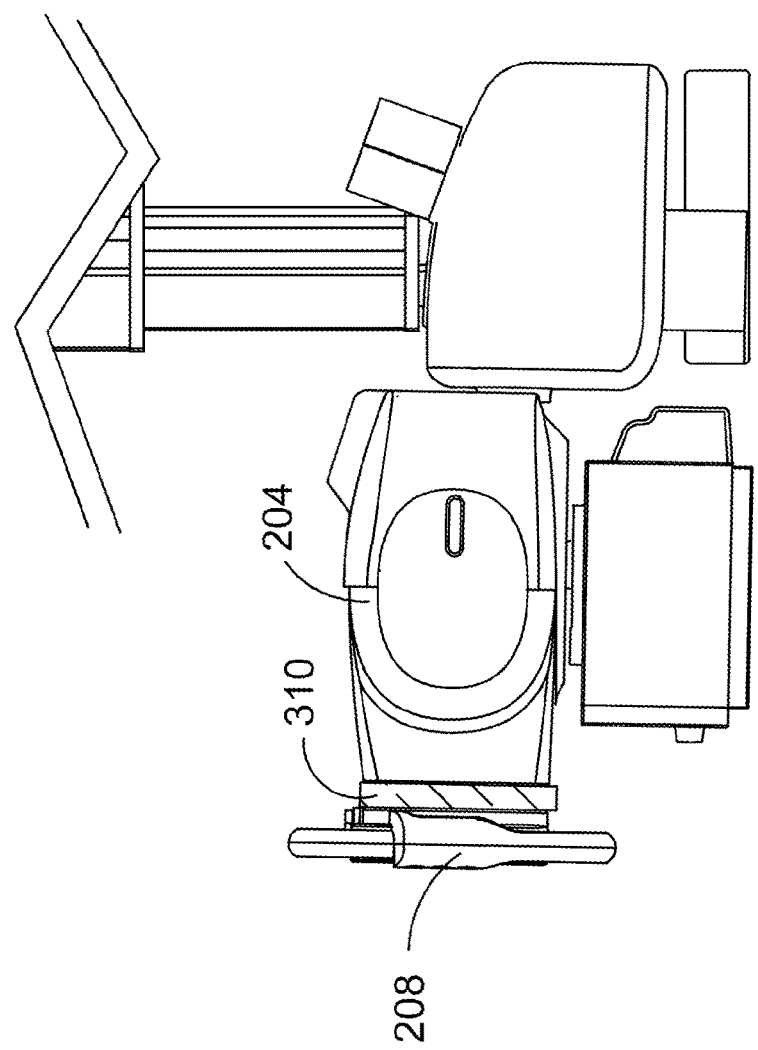
FIG. 4 is a schematic diagram of the position of a measurement device in the assistance system shown in FIG. 3.

FIG. 2 shows a schematic diagram of a suspension device 200 according to some embodiments of the present invention. FIG. 4 shows a schematic diagram of an assistance system 300 for a suspension system according to some embodiments of the present invention. As shown in FIG. 2 and FIG. 3, the suspension device 200 includes a transverse guide rail 201, a longitudinal guide rail 203, a retractable tube 202, a tube device 204, a beam limiter 206 and a tube controller 208.

For ease of description, in the present application, the x-axis, y-axis and z-axis are defined as that the x-axis and y-axis are located in a horizontal plane and perpendicular to each other, and the z-axis is perpendicular to the horizontal plane. Specifically, in a first coordinate system using the room as a reference, the direction in which the transverse guide rail 201 is located is defined as the x-axis, the direction in which the longitudinal guide rail 203 is located is defined as the y-axis direction, and the extension direction of the retractable tube 202 is defined as the z-axis direction, and the z-axis direction is a vertical direction. In addition, the movement of the suspension device further includes rotation of the tube device 204 in a vertical plane and rotation of the tube device 204 in a horizontal plane. That is, when the tube device 204 rotates in the vertical plane, the tube device rotates around the y-axis, and the angle of rotation of the tube device 204 with respect to the initial position is defined as a first rotation angle α. When the tube device 204 rotates in the horizontal plane, the tube device rotates around the z-axis, and the angle of rotation of the tube device 204 with respect to the initial position is defined as a second rotation angle θ. For ease of display, bellows are omitted in FIG. 2.

Specifically, the transverse guide rail 201 is disposed on a ceiling. The longitudinal guide rail 203 is disposed on the transverse guide rail 201, and is perpendicular to the transverse guide rail 201. The retractable tube 202 is a telescopic tube, and one end of the retractable tube is connected to the longitudinal guide rail 203, and the other end is connected to the tube device 204, or is connected to the tube device 204 by means of a rotating member (not shown in the figure). The retractable tube 202 can move relative to the longitudinal guide rail 201 so as to drive the retractable tube 202 to move in the y-axis direction. The longitudinal guide rail 201 can move relative to the transverse guide rail 201 so as to drive the retractable tube 202 to move in the x-axis direction.

The suspension device 202 includes a plurality of sleeves (or housings) having different inner diameters, and the plurality of sleeves may be sequentially sleeved, from bottom to top, in sleeves located thereon to achieve extension or retraction, such that the retractable tube 202 or the tube device 204 can move in the z-axis direction. Specifically, a connection portion between the suspension device 202 and the longitudinal guide rail 203 may include components such as a rotating shaft, a motor, and a reel. The motor can drive the reel to rotate around the rotating shaft so as to drive the retractable tube 202 to move along the z-axis.

The suspension device 200 further includes a motion driving device 210. The motion driving device 210 comprises a motor driver and a plurality of motors. The plurality of motors are used to control movements of the suspension device in the first coordinate system, including movements along the x-axis, y-axis, and z-axis, respectively.

Specifically, for controlling the motion of the suspension device along the x-axis, the motion driving device 210 includes an x-axis motor driver 211, an x-axis motor 221, and an x-axis feedback unit 231. Similarly, for controlling the motion of the suspension device along the y-axis, the motion driving device 210 includes a y-axis motor driver 212, a y-axis motor 222, and a y-axis feedback unit 232, and for controlling the motion of the suspension device along the z-axis, the motion driving device 210 includes a z-axis motor driver 213, a y-axis motor 223, and a z-axis feedback unit 233. The x/y/z-axis motor driver can control the x/y/z-axis motor to rotate on the basis of a command of the controller to drive the suspension device to move along the x/y/z-axis, while the x/y/z-axis feedback unit can monitor the speed and position of the suspension device in real time, so as to provide real-time feedback. Specifically, the x/y/z-axis feedback unit includes an encoder and a potentiometer.

Of course, the motion driving device may further include other components for achieving motion, such as reels, synchronous wheels and wire ropes.

Specifically, the motion driving device includes an automatic mode (also known as a position mode) and an assistance mode (also known as a torque mode). In the automatic mode, the motor driver can drive the corresponding motor to rotate until a predetermined position is reached, while in the assistance mode, the motor driver can drive the corresponding motor to rotate according to a torque value.

The motion driving device 210 can be provided in a connection portion 205 between the retractable tube 202 and the guide rails 201/203. The specific location and/or manner of installation of the motion driving device and unnecessary details as to how to automatically control the movement of the suspension device along the three axes will not be described herein.

Although the motion driving device 210 is shown in some embodiments of the present invention to include three motor drivers, it should be understood by those skilled in the art that it is also possible to provide only one motor driver for general control of the motors of the three axes to carry out the operations.

The suspension device 200 further includes the assistance system 300, and the assistance system 300 includes a measurement device 310 and a control device 320.

FIG. 4 illustrates a schematic diagram of the position of the measurement device in the assistance system 300 shown in FIG. 3. As shown in FIG. 4, the measurement device 310 is disposed between the tube device 204 and the tube controller 208 so as to obtain an initial force of an operator, wherein the initial force includes the magnitude and direction of a force along a second coordinate system in which the measurement device 310 is located.

In some embodiments, the measurement device 310 is a three-dimensional sensor that can measure the magnitude and direction of the force applied thereon.

Specifically, the coordinate system in which the length, width and height of the measurement device 310 are located is defined as the second coordinate system, and when the suspension device is in a default position as shown in FIG. 2, the first and second coordinate systems overlap. However, during an actual examination scan, depending on the examination protocol or region of the object under examination, etc., it is usually necessary to move and/or rotate the suspension device to a predetermined position and/or angle, so that the tube can align with the region of interest of the object under examination. That is, the tube device 204 will have a certain rotation around the y-axis or z-axis, and the first coordinate system and the second coordinate system will also have a certain degree of deviation or rotation. If the motion driving device provides assistance directly on the basis of the torque of the three-dimensional force obtained from the measurement device, such control will have a large degree of deviation, and the assistance system cannot provide assistance in the direction of the operator's movement.

Referring back to FIG. 2, in some embodiments, the control device 320 includes a calibration unit 321 and a calculation unit 322. The calibration unit 311 is used for calibrating an initial force F to obtain a calibrated force F0. The calculation unit 322 is used for performing a coordinate transformation on the calibrated force F0 to obtain a torque value corresponding to a first coordinate system, and sending the torque value to the motion driving device to enable the motion driving device to provide assistance on the basis of the torque value.

The calibration unit 311 is further used for calibrating the initial force on the basis of the current first rotation angle α and the current second rotation angle θ and according to a look-up table so as to obtain the calibrated force F0. The first rotation angle is the angle of rotation of the tube in a vertical plane and the second rotation angle is the angle of rotation of the tube in a horizontal plane.

In some embodiments, since the tube device 204 will have a certain rotation around the y-axis or z-axis, and since the measurement device is connected between the tube device and the tube controller, when the tube device is rotated, the tube controller or other components will exert pressure on the measurement device due to their own gravity, so that the force obtained by the measurement device is not merely the operating force of the operator. Thus, during the experimental or installation test phase, measured values of the measurement device at different first and second rotation angles are recorded without applying an external force, so as to obtain the aforementioned look-up table. In some non-limiting embodiments, the values of the measurement device may be recorded at every 5° interval in each direction of the tube device, and of course, for more precise control, the angle intervals may be configured to be smaller.

The aforementioned look-up table may be stored in a storage device or the calibration unit 321 in the X-ray imaging system. During an actual examination, the measured values corresponding to the first rotation angle and the second rotation angle recorded by the X-ray imaging system may be obtained after the positioning operation is completed, and the calibration unit 321 can then calibrate the initial force F on the basis of the corresponding measured values obtained from the look-up table to obtain the magnitude and direction of the force actually applied to the suspension device by the operator, thereby achieving a more accurate control.

Although the above embodiment describes the calibration of the initial force obtained by the measurement device by means of a look-up table, it should be understood by those skilled in the art that other schematic means of calibrating the initial force may also be used, for example, by means of formula calculations, etc.

In some embodiments, the calculation unit 322 is used for performing a coordinate transformation on the basis of the positional relationship between the first coordinate system and the second coordinate system.

Specifically, the positional relationship between the first coordinate system and the second coordinate system includes a matrix related to the first rotation angle and the second rotation angle.

Specifically, the magnitude and direction of the initial force measured by the measurement device is based on the second coordinate system in which the measurement device is located, while the x/y/z axis motors, motor drivers, etc. are based on the first coordinate system in which the room is located. Thus, a positional relationship between the first and second coordinate systems may be obtained on the basis of the matrix between the first and second rotation angles, and then the magnitude and direction of the calibrated force in the second coordinate system are converted to the magnitude and direction of the force corresponding to the first coordinate system, and then the corresponding torque values are sent to the x/y/z axis motor drivers, respectively, such that the x/y/z axis motors can be controlled to rotate to provide assistance in the direction desired by the operator.

In some embodiments, the torque value includes the product of a force obtained after a coordinate transformation and a multiplier, the multiplier being adjustable. Specifically, in an X-ray imaging system, by providing different multiplier options, a user may make a selection according to actual needs so as to adjust the sensitivity of the assistance system. The multiplier in the system is predetermined to provide better user experience. However, if the user desires to achieve accurate movement of small distances, then a smaller multiplier may be selected, and if the user desires to move the suspension device with only a small force, then a larger multiplier may be selected, thereby providing the user with personalized customization through such adjustable multipliers.

In some embodiments, the calculation unit may send a torque value to the corresponding motor driver (or motion driving device) on the basis of the communication link shown in FIG. 1. Specifically, the communication link includes a CAN bus.

In some embodiments, the calculation unit 322 is further used for performing slope-limiting on the transformed force obtained after the coordinate transformation, and the torque value includes the product of the slope-limited force and a multiplier.

Specifically, the aforementioned slope-limiting refers to limiting a force having an amplitude (or magnitude) of change per unit time that exceeds a threshold.

By performing slope-limiting on the transformed force obtained after the change of the coordinates, a force with a change per unit time that exceeds a threshold can be removed or limited. On the one hand, it is possible to prevent the assistance system from providing assistance due to any external momentary force when the suspension device encounters any external interference or collision, and on the other hand, it is possible to provide stable and smooth assistance if any extreme or uneven force is applied by the user.

In some embodiments, the calibration unit 321 may further include limiting the calibrated force on the basis of a real-time feedback value of the motion driving device and performing a coordinate transformation on the limited calibrated force, and the real-time feedback value includes at least one of the movement speed and position of the suspension device.

Specifically, the x/y/z-axis feedback unit can provide real-time feedback on the speed and position of the suspension device. By sending the real-time feedback information on speed and position to the calibration unit, the calibration unit can limit the calibrated force on the basis of the real-time feedback on speed and position. For example, when the suspension device is about to reach a limit position (the position of the two ends of the guide rail) or when the speed is too fast, if the initial force applied by the operator on the suspension device is still large at this point, the assistance system will reduce the torque sent to the motion driving device accordingly, so as to reduce the speed of the suspension device in order to avoid collision due to excessive speed.

Figure 5:
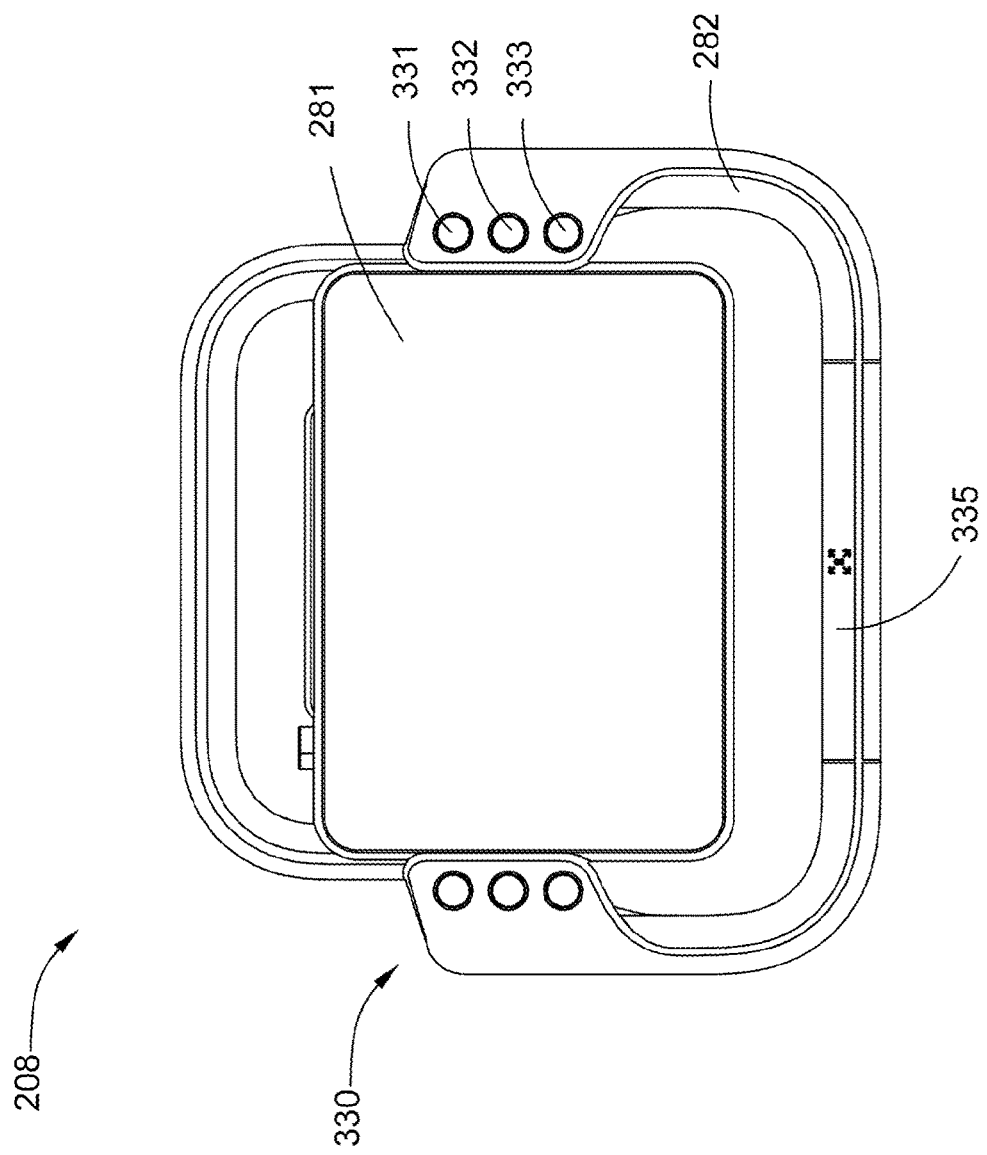
FIG. 5 is a schematic diagram of a mode-switching device in the assistance system shown in FIG. 3.

FIG. 5 illustrates a schematic diagram of the mode-switching device in the assistance system shown in FIG. 4. As shown in FIG. 5, the assistance system 300 further includes a mode-switching device 300. The mode-switching device 330 is located on the tube controller 208 to switch the motion driving device between the automatic mode and the assistance mode.

Specifically, the tube controller 208 includes a display screen 281 and an operating handle 282.

In some embodiments, the mode-switching device includes a plurality of switch buttons 331/332/333, and the plurality of switch buttons respectively correspond to movements along respective axes in the first coordinate system, so as to perform switching from the automatic mode to the assistance mode. The other control buttons shown in the figure may be used for performing pre-scan preparations such as patient selection, protocol selection, and positioning, etc.

The plurality of switch buttons are provided on the operating handle 282 and near the end of the display screen 281. Of course, the plurality of switch buttons may also be disposed on the display screen.

Specifically, the first switch button 331 is used for controlling the movement of the suspension device along the x-axis, i.e., the first switch button 331 may switch the x-axis motor from the automatic mode to the assistance mode. The second switch button 332 is used for controlling the movement of the suspension device along the y-axis, i.e., the second switch button 332 may switch the y-axis motor from the automatic mode to the assistance mode. The third switch button 333 is used for controlling the movement of the suspension device along the z-axis, i.e., the third switch button 333 may switch the z-axis motor from the automatic mode to the assistance mode.

Although a plurality of switch buttons shown in FIG. 5 are on the same side of the display screen, it should be understood by those skilled in the art that the plurality of switch buttons may be disposed in any suitable order or position, e.g., all are disposed on the left, or some on the left and some on the right. In addition, although six switch or control buttons are disposed symmetrically as shown in the figure, the number and position of the disposed switch or control buttons are not fixed.

In some embodiments, the mode-switching device 330 further includes at least one sensor 335, and the at least one sensor 335 is provided at the bottom of the display screen 281 or on the operating handle 282 to switch the motion driving device from the automatic mode to the assistance mode when the operator operates the operating handle 282.

Specifically, the sensor 335 may be disposed on the bottom of the display screen or on the operating handle, and is used to switch to the assistance mode on the basis of sensing the hand of the operator. In a non-limiting embodiment, the sensor may be an infrared sensor or a camera and so on.

In some embodiments, the x-axis motor, y-axis motor and z-axis motor are all switched to the assistance mode when the user operates the operating handle 282.

In some embodiments, each of the plurality of switch buttons 331/332/333 includes an indicator light. When at least one of the switch buttons is pressed by an operator, the indicator light illuminates or changes color to indicate such pressing, and when the operation handle 282 is operated by an operator, all of the indicator lights of the plurality of switch buttons illuminate or change color to indicate such operation, i.e., the movements along all three axes are switched to the assistance mode.

Specifically, the motion driving device (or motor) can only be switched to the assistance mode to provide assistance to the user when the user operates the tube controller (the switch button or operating handle), rather than on the basis of the fact that the measurement device has measured a force, thereby preventing the motion driving device from switching to the assistance mode when the measurement device measures some unintended force or some force unrelated to operation.

When the user operates the tube controller, the controller or workstation can send commands to the motor driver of the corresponding axis by means of a communication link, so as to switch to the assistance mode.

Figure 6:
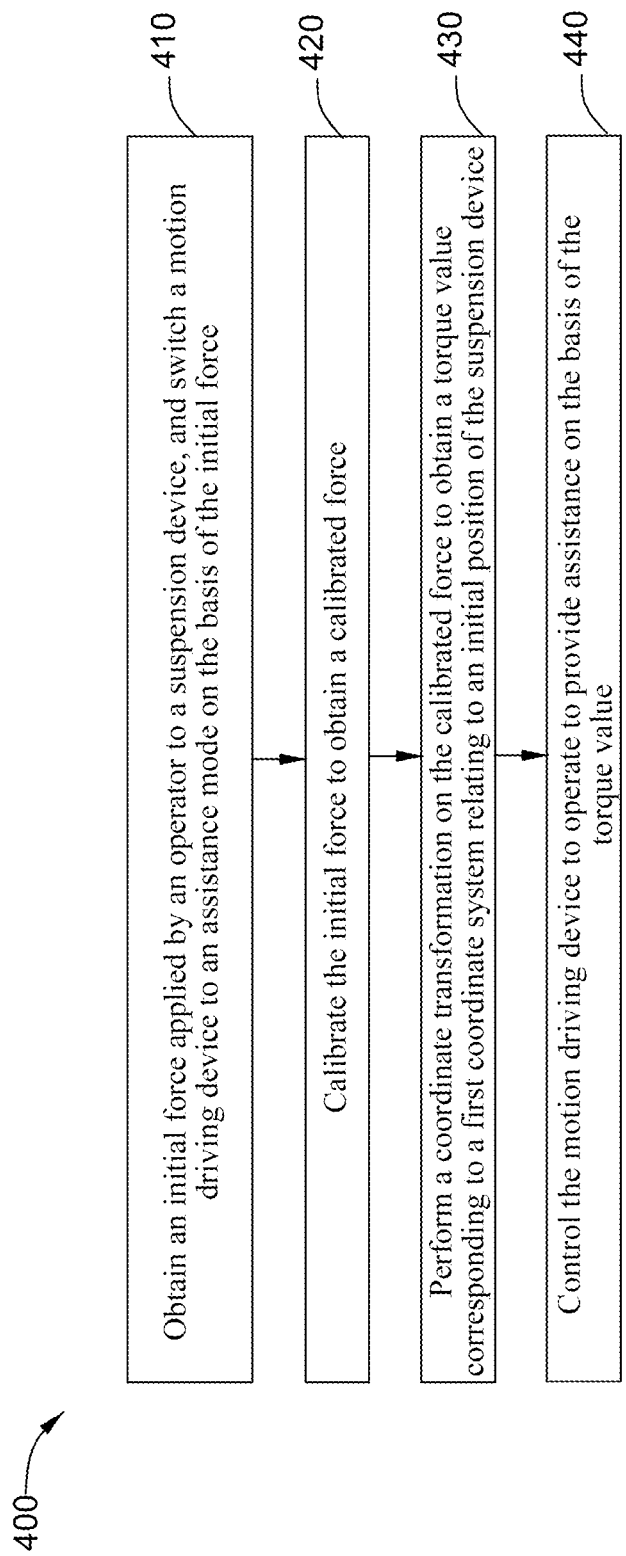
FIG. 6 is a flowchart of an assistance method for a suspension device according to some embodiments of the present invention.

FIG. 6 shows a flowchart of an assistance method 400 for a suspension device according to some embodiments of the present invention. As shown in FIG. 6, the assistance method 400 for a suspension device includes step 410, step 420, step 430 and step 440.

In step 410, an initial force applied to a suspension device by an operator is obtained, and a motion driving device is switched to an assistance mode on the basis of the initial force.

In some embodiments, when a user operates a switch button on the tube controller, the motor of the axis corresponding to the control of the switch button is switched to the assistance mode and assistance is provided to the user with respect to on that axis. When a user operates the operating handle on the tube controller, the motors of all three axes are all switched to the assistance mode, and the user is given assistance with respect to the corresponding axis on the basis of the magnitude and direction of the initial force obtained by the measurement device. In the assistance mode, the motor may rotate on the basis of a corresponding torque value.

In step 420, the initial force is calibrated to obtain a calibrated force.

In some embodiments, the calibration includes calibrating the initial force on the basis of a current first rotation angle α and a current second rotation angle θ of the suspension device and according to a look-up table.

Specifically, the look-up table is obtained by recording measured values of the measurement device at different first and second rotation angles without applying an external force during the experimental or initial stage. In some non-limiting embodiments, the values of the measurement device may be recorded at every 5° interval in each direction of the tube device, and of course, for more precise control, the angle intervals may be configured to be smaller.

In step 430, a coordinate transformation is performed on the calibrated force to obtain a torque value corresponding to the first coordinate system relating to an initial position of the suspension device.

In some embodiments, the coordinate transformation includes a coordinate transformation performed on the basis of a positional relationship between the first coordinate system and the second coordinate system. Specifically, the positional relationship between the first coordinate system and the second coordinate system includes a matrix related to the first rotation angle and the second rotation angle.

Specifically, the matrix between the first rotation angle and the second rotation angle may be obtained using the sizes of the current first rotation angle and the current second rotation angle of the suspension device known in the system, then the positional relationship between the first coordinate system and the second coordinate system may be obtained, and then the magnitude and direction of the calibrated force in the second coordinate system are converted to the magnitude and direction of the force corresponding to the first coordinate system, and then the corresponding torque values can be sent to the motor drivers respectively, so as to control the motor of the corresponding axis to rotate in order to provide assistance in the direction desired by the operator.

In some embodiments, obtaining the torque value includes multiplying the force obtained after the coordinate transformation and a multiplier, wherein the multiplier is adjustable. By adjusting the multiplier in the torque value, the sensitivity of the assistance system may be adjusted to improve the user experience.

In step 440, the motion driving device is controlled to operate to provide assistance on the basis of the torque value.

Figure 7:
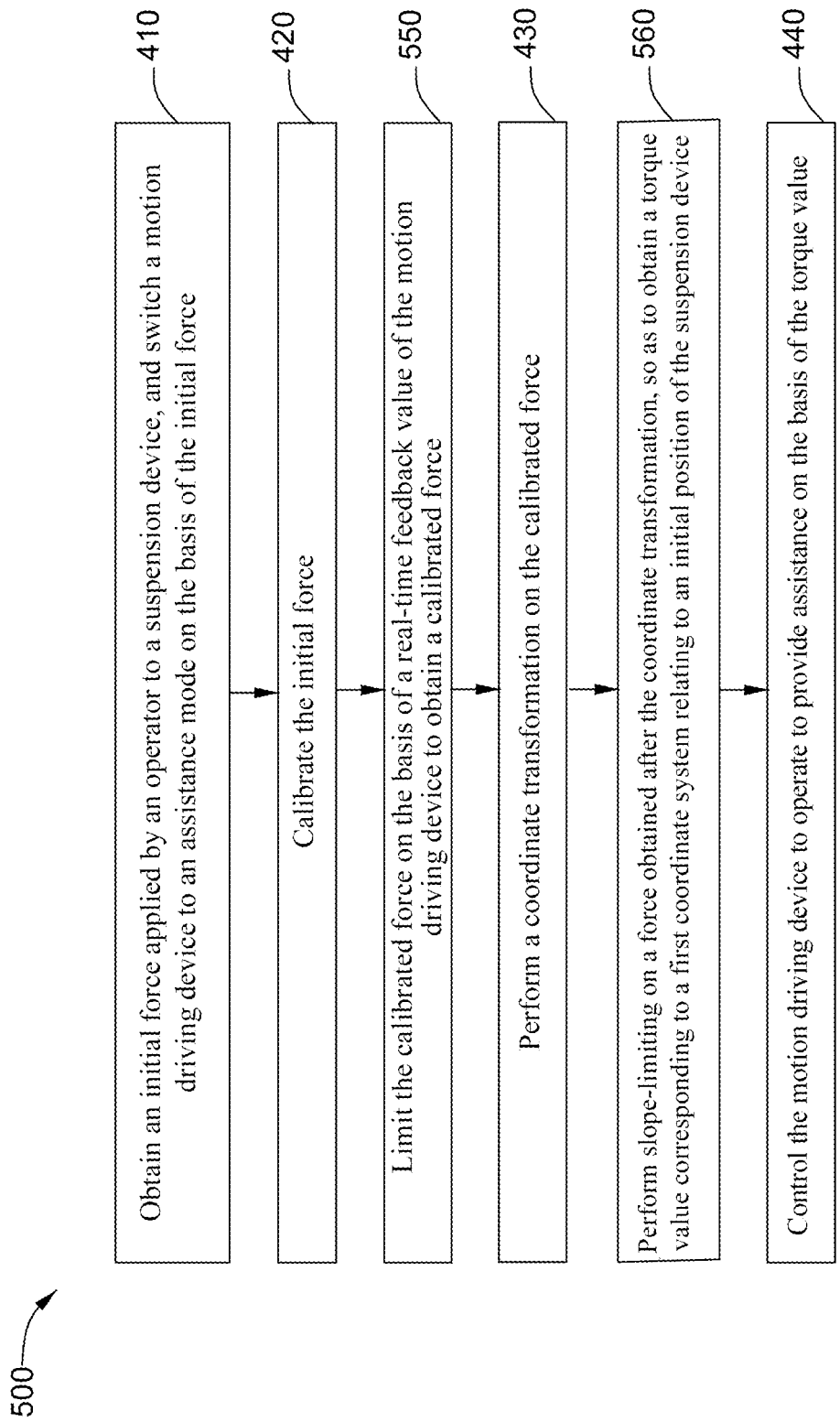
FIG. 7 is a flowchart of an assistance method for a suspension device according to some other embodiments of the present invention.

FIG. 7 shows a flowchart of a suspension device assistance method 500 according to some other embodiments of the present invention. Unlike the assistance method 400 shown in FIG. 6, the assistance method 500 shown in FIG. 7 further includes steps 550 and 560.

After step 420 in which the processing force is calibrated, step 550 is further included. In step 550, the calibrated force is limited on the basis of a real-time feedback value from the motion driving device, and a coordinate transformation is performed on the limited calibrated force.

Specifically, the real-time feedback value includes at least one of the movement speed and position of the suspension device. Specifically, when the suspension device is about to reach the limit position (the position of the two ends of the guide rail) or when the speed is too fast, if the initial force applied by the operator on the suspension device is still large, the assistance system will reduce the torque sent to the motion driving device accordingly so as to reduce the speed of the suspension device in order to prevent any collision due to excessive speed.

After step 430 in which a coordinate transformation of the calibrated force is performed, step 560 is further included. In step 560, slope-limiting is performed on the transformed force obtained after the coordinate transformation, and the torque value includes the product of the force obtained after the slope-limiting and a multiplier.

Specifically, the aforementioned slope-limiting refers to limiting a force having an amplitude (or magnitude) of change per unit time that exceeds a threshold. By performing slope-limiting on the transformed force obtained after the change of the coordinates, on the one hand, it is possible to remove a force with a change per unit time that exceeds a threshold in order to prevent the assistance system from providing assistance due to an external momentary force if the suspension device encounters any external interference or collision, and on the other hand, when a user operates the suspension device using an extreme force, it is possible to allow the assistance system to provide assistance in a stable manner or at a stable speed to achieve smooth and safe control or operation.

In the assistance system for the suspension device according to some embodiments of the present invention, firstly, the magnitude and direction of the force applied by the operator are obtained by a measurement device, and a coordinate transformation is performed on the force obtained by the measurement device, which is then transformed into a torque value for the motors corresponding to the three axes of the room-based coordinate system on the basis of the angle of rotation of the tube device, so that the motors can provide assistance in the direction desired by the operator. Secondly, the force obtained by the measurement device is calibrated through a look-up table to obtain the magnitude and direction of the force applied to the suspension device by the operator, thereby preventing the pressure generated by the tube controller on the measurement device from influencing the magnitude and direction of the initial force, so as to achieve more accurate control. Further, by limiting the calibrated force on the basis of the real-time feedback of the speed and position, the speed of the suspension device can be reduced when the suspension device is about to reach a limit position or when the speed is too fast, so as to prevent any collision due to excessive speed. Furthermore, by performing slope-limiting on the transformed force obtained after the change of the coordinates, the assistance system can be prevented from providing assistance due to any external momentary force when the suspension device encounters any external interference or collision. Finally, by setting the multiplier for obtaining the torque value to be adjustable, a user may select different multipliers to adjust the sensitivity of the assistance system, which can improve the user experience. All in all, the assistance system of the present application does not require structural or hardware changes to the motion driving device except for the installation of a measurement device in the tube and the tube controller, thereby reducing costs.

As used herein, the term "computer" may include any processor-based or microprocessor-based system that includes a system using a microcontroller, a reduced instruction set computer (RISC), an application specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above, however, it should be understood that various modifications may be made. For example, suitable results can be achieved if the described techniques are performed in different orders and/or if components in the described systems, architectures, devices, or circuits are combined in different ways and/or replaced or supplemented by additional components or equivalents thereof. Accordingly, other implementations also fall within the protection scope of the claims.

The invention claimed is:

1. An assistance system for a suspension device, the suspension device comprising a tube device, a tube controller and a motor driver, the motor driver device being capable of driving the suspension device to move along a first coordinate system, and the assistance system comprising: a sensor disposed between the tube device and the tube controller so as to obtain an initial force of an operator, wherein the initial force comprises a magnitude and direction of a force along a second coordinate system in which the sensor is located; and a controller configured to, calibrate the initial force to obtain a calibrated force, perform a coordinate transformation on the calibrated force to obtain a torque value corresponding to the first coordinate system,
 perform slope-limiting on a transformed force obtained after the coordinate transformation, and the torque value comprises the product of a force obtained after the slope-limiting and a multiplier, and send the torque value to the motor driver to enable the motor driver to provide assistance on the basis of the torque value.

2. The assistance system according to claim 1, wherein the moto driver comprises an automatic mode and an assistance mode, and the assistance system further comprises a mode-switching device disposed on the tube controller and used to switch the motor driver between the automatic mode and the assistance mode.

3. The assistance system according to claim 2, wherein the mode-switching device comprises a plurality of switch buttons, and the plurality of switch buttons respectively correspond to movements along respective axes in the first coordinate system, so as to perform switching from the automatic mode to the assistance mode.

4. The assistance system according to claim 3, wherein the tube controller comprises a display screen and an operating handle, and the mode-switching device further comprises at least one sensor disposed at the bottom of the display screen or on the operating handle to switch the motor driver from the automatic mode to the assistance mode when the operator operates the operating handle.

5. The assistance system according to claim 2, wherein each of the plurality of switch buttons comprises an indicator light, and when at least one of the switch buttons is pressed by an operator, the indicator light illuminates to indicate such pressing, and when the operating handle is operated by an operator, all of the indicator lights of the plurality of switch buttons illuminate to indicate such operation.

6. The assistance system according to claim 1, wherein the controller is further configured to calibrate the initial force on the basis of a current first rotation angle and a current second rotation angle and according to a look-up table, so as to obtain the calibrated force, the first rotation angle being an angle at which the tube rotates in a vertical plane, and the second rotation angle being an angle at which the tube rotates in a horizontal plane.

7. The assistance system according to claim 6, wherein the control device is further configured to limit the calibrated force on the basis of a real-time feedback value of the motor driver, and performing a coordinate transformation on the limited calibrated force, the real-time feedback value comprising at least one of a movement speed and a position of the suspension device.

8. The assistance system according to claim 1, wherein the controller is further configured to perform a coordinate transformation on the basis of a positional relationship between the first coordinate system and the second coordinate system.

9. The assistance system according to claim 8, wherein the positional relationship between the first coordinate system and the second coordinate system comprises a matrix related to a first rotation angle and a second rotation angle.

10. The assistance system according to claim 1, wherein the torque value comprises the product of a force obtained after a coordinate transformation and a multiplier, the multiplier being adjustable.

11. An X-ray imaging system, comprising the assistance system for the suspension device according to claim 1.

12. An assistance method for a suspension device, the suspension device comprising a motor driver, and the assistance method comprising:

obtaining an initial force applied by an operator to the suspension device, and switching the motor driver to an assistance mode on the basis of the initial force;

calibrating the initial force to obtain a calibrated force;

performing a coordinate transformation on the calibrated force to obtain a torque value corresponding to a first coordinate system relating to an initial position of the suspension device;

performing slope-limiting on a transformed force obtained after the coordinate transformation, and the torque value comprises the product of a force obtained after the slope limiting and a multiplier; and controlling the motor driver to operate to provide assistance on the basis of the torque value.

* * * * *